United States Patent [19]
Armentrout et al.

[11] Patent Number: 5,736,015
[45] Date of Patent: Apr. 7, 1998

[54] ELECTRICAL DISCHARGE MACHINING APPARATUS

[75] Inventors: Charles Armentrout, Ann Arbor; Lesley A. Calvert, Munith; Lawrence Davies, Ann Arbor; John Jarchow; Michael Pulka, both of Jackson; Jon Thomson, Grass Lake, all of Mich.

[73] Assignee: Pilot Industries, Inc., Dexter, Mich.

[21] Appl. No.: 709,388

[22] Filed: Sep. 6, 1996

[51] Int. Cl.$^6$ .................... B23H 7/00; B23H 7/26
[52] U.S. Cl. .................. 204/224 M; 204/225; 219/69.11
[58] Field of Search .................... 204/225, 224 M, 204/238; 205/654, 686; 219/69.11

[56] References Cited

U.S. PATENT DOCUMENTS

| | | | |
|---|---|---|---|
| 2,385,198 | 9/1945 | Engle | 204/224 M X |
| 2,650,979 | 9/1953 | Teubner | 204/224 M |
| 3,239,438 | 3/1966 | Voorhees | 204/224 M X |
| 3,293,163 | 12/1966 | O'Connor | 205/654 X |
| 4,363,627 | 12/1982 | Windeler | 219/69 M X |
| 4,734,173 | 3/1988 | Walter et al. | 204/225 X |

*Primary Examiner*—Donald R. Valentine
*Attorney, Agent, or Firm*—Gifford, Krass, Groh, Sprinkle, Patmore, Anderson & Citkowski, P.C.

[57] ABSTRACT

An electrical discharge machining apparatus is disclosed having a frame with a base and a vertical support secured to and extending upwardly from the base. A tank adapted to contain an electrolytic liquid is secured to the vertical support by an adjustment mechanism which enables the vertical position of the tank to be varied. A work holder is optionally pivotally secured to the top of the vertical support and movable between a work position in which the work support and work are aligned with the tank and an inspection position in which the work holder is laterally spaced from the tank. Electrical discharge electrodes are contained within the tank while a servo motor vertically moves the work support with its attached work against the electrodes to perform the machining operation. The electrical discharge apparatus is particularly suited for dental prosthesis applications.

18 Claims, 5 Drawing Sheets

ELECTRICAL DISCHARGE MACHINING APPARATUS

BACKGROUND OF THE INVENTION

I. Field of the Invention

The present invention relates to an electrical discharge machining apparatus and, more particularly, to such an apparatus particularly suitable for use in dental bridgework applications.

II. Description of the Prior Art

There are many previously known electrical discharge machining apparatuses that are used in a variety of different applications. Typically, the previously known apparatus includes a first work tank filled with electrolytic liquid and in which the work is mounted as well as a second reservoir tank for the fluid. Electrical discharge electrodes are then moved against the work contained within the tank and ablate material from the work for each electrical discharge.

Although electrical discharge machining apparatuses have been used in many different applications, none to date have been specifically adapted for use for dental applications. In particular, in order to secure a dental prosthesis, such as bridgework, to the jaw of a patient, threaded metal pins are typically planted into the jaw so that the pins protrude slightly upwardly through the patient's gum and into the patient's mouth. The dental prosthesis then includes mounting surfaces which register with the tops of the pins so that, when the dental prosthesis is positioned on the pins, threaded fasteners can be used to secure the prosthesis in place.

In securing a dental prosthesis to the patient's mouth in the above-described fashion, it is absolutely essential that the mounting surfaces in the prosthesis properly mate with the tops of the pins contained in the patient's mouth. Otherwise, once the prosthesis is secured to the pins by threaded fasteners, longitudinal stresses can be imposed between the pins which can be and often is very painful to the patient. Furthermore, even if not painful, the prosthesis may eventually break unless properly mated with the pins.

In order to prevent the longitudinal stress which can be caused by improperly formed mating surfaces in the prosthesis, the dentist must manually form the mating surfaces on the prosthesis and modify the surfaces until all longitudinal stress between the pins is eliminated. This is time consuming and, therefore, expensive.

It is well known that EDM devices are capable of machining accurate holes in metal work pieces. Such EDM machinery, however, has not been previously used in dental applications, especially in prosthesis applications, since the work has been contained within the EDM tank which cannot be easily viewed by the dentist through the electrolytic liquid.

SUMMARY OF THE PRESENT INVENTION

The present invention provides an EDM device which overcomes all of the above-mentioned disadvantages of the previously known devices and is particularly suitable for use in dental applications for machining prostheses.

In brief, the EDM device of the present invention comprises a frame having a base and a vertical support secured to and extending upwardly from the base. A tank is secured to the vertical support by an adjustable mechanism which adjustably vertically displaces the tank along the vertical support. The tank is filled with an electrolytic liquid in the conventional fashion.

The prosthesis to be machined is secured to the work holder in any conventional fashion. Once the set up is completed, the tank is raised so that the prosthesis is submerged in the electrolytic fluid.

A servo motor is operatively coupled to the work holder so that, upon activation, the servo motor moves the work holder along an axis aligned with the tank when the work holder is in its operable position. A mechanical adjusting plate is also provided between the work holder and the servo motor for displacing the work holder in directions lateral to its longitudinal axes.

In practice, electrodes are contained within the tank and in alignment with work, such as a dental bridge or other prosthesis, secured to the work holder. Activation of the servo motor then moves the work into the tank and against the electrodes to perform the machining operation, e.g. the modification of the tops of the holes so they are properly seated.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
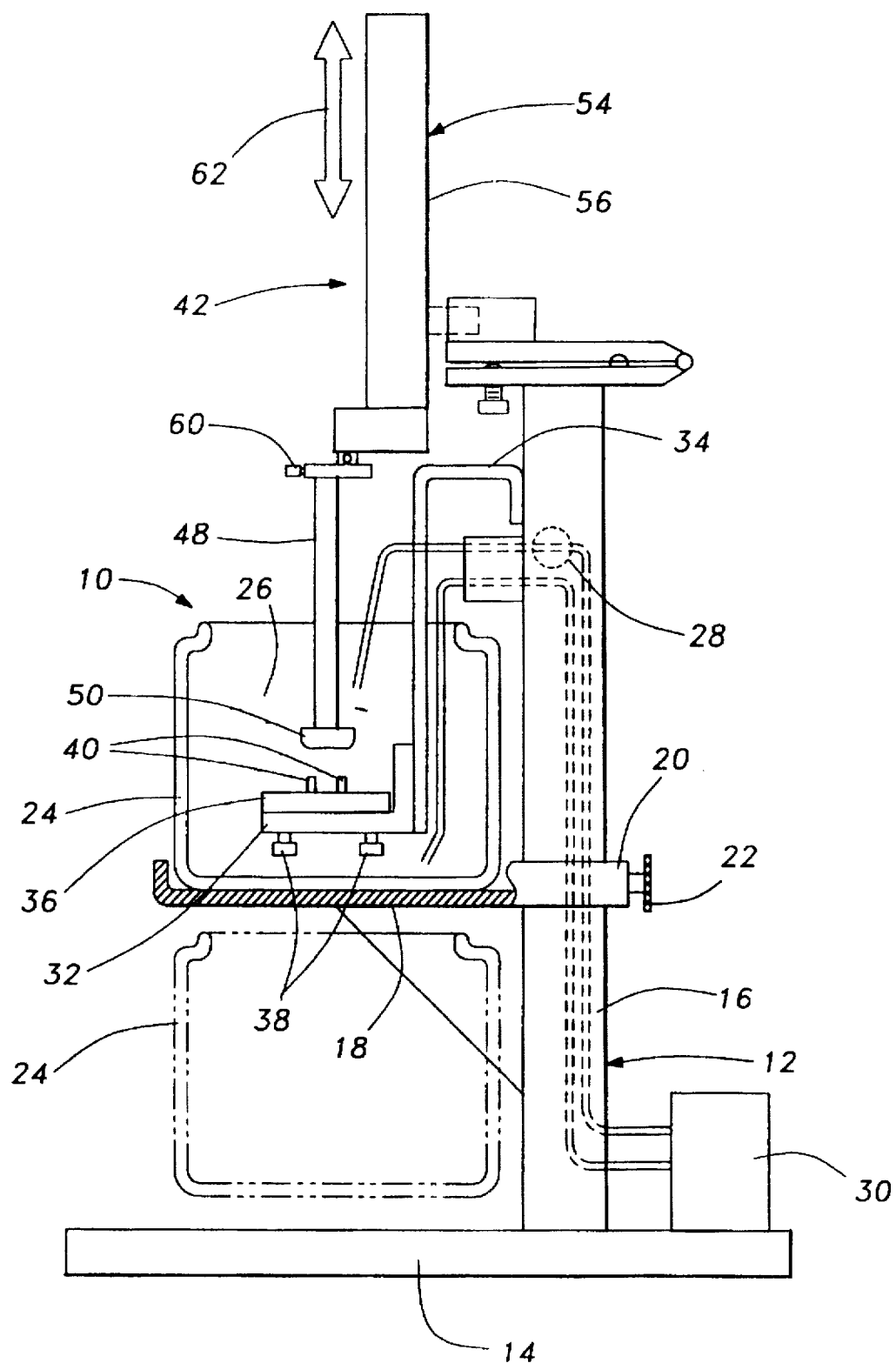
FIG. 1 is a side diagrammatic view illustrating a preferred embodiment of the present invention in an operable position.

With reference first to FIG. 1, a first preferred embodiment of the electrical discharge machining (EDM) apparatus 10 of the present invention is there shown and comprises a frame 12 having a base 14. An elongated vertical support 16 has its lower end secured to the base 14 such that the vertical support 16 extends vertically upwardly from the base 14.

A generally planar table 18 includes a throughbore 20 at one end that is longitudinally slidably mounted to the vertical support 16. A threaded knob 22 is threadably secured to the table 18 and abuts against the vertical support 16. Thus, tightening the knob 22 locks the vertical position of the table 18 relative to the vertical support 16 while loosening the knob 22 allows the vertical position of the table 18 to be vertically adjusted. A pawl and ratchet mechanism can alternatively be used to adjust the vertical position of the table 18.

A tank 24 is supported by an upper surface of the table 18. The tank 24 is designed to contain a conventional electrolytic liquid.

In order to filter debris from the liquid 26 contained within the tank 24, a liquid pump 28 has its outlet open to the interior of the tank 24. A liquid filter 30 is then contained fluidly in series between the inlet of the pump 28 and the interior of the tank 24. Consequently, upon activation of the pump 28, the pump 28 inducts the electrolytic liquid 26 from the tank 24, cleans the liquid by the filter 30 and then returns the cleaned liquid back to the tank 26.

Still referring to FIG. 1, a support 32 is secured to the vertical support 16 by a bracket 34 so that, with the table 18 in the position illustrated in FIG. 1, the angle support 32 is contained within the interior of the tank 24 adjacent its bottom. A plate 36 is adjustably secured to the angle mount 32 by adjustment screws 38 and EDM electrodes 40 are carried by the plate 36.

Figure 2:
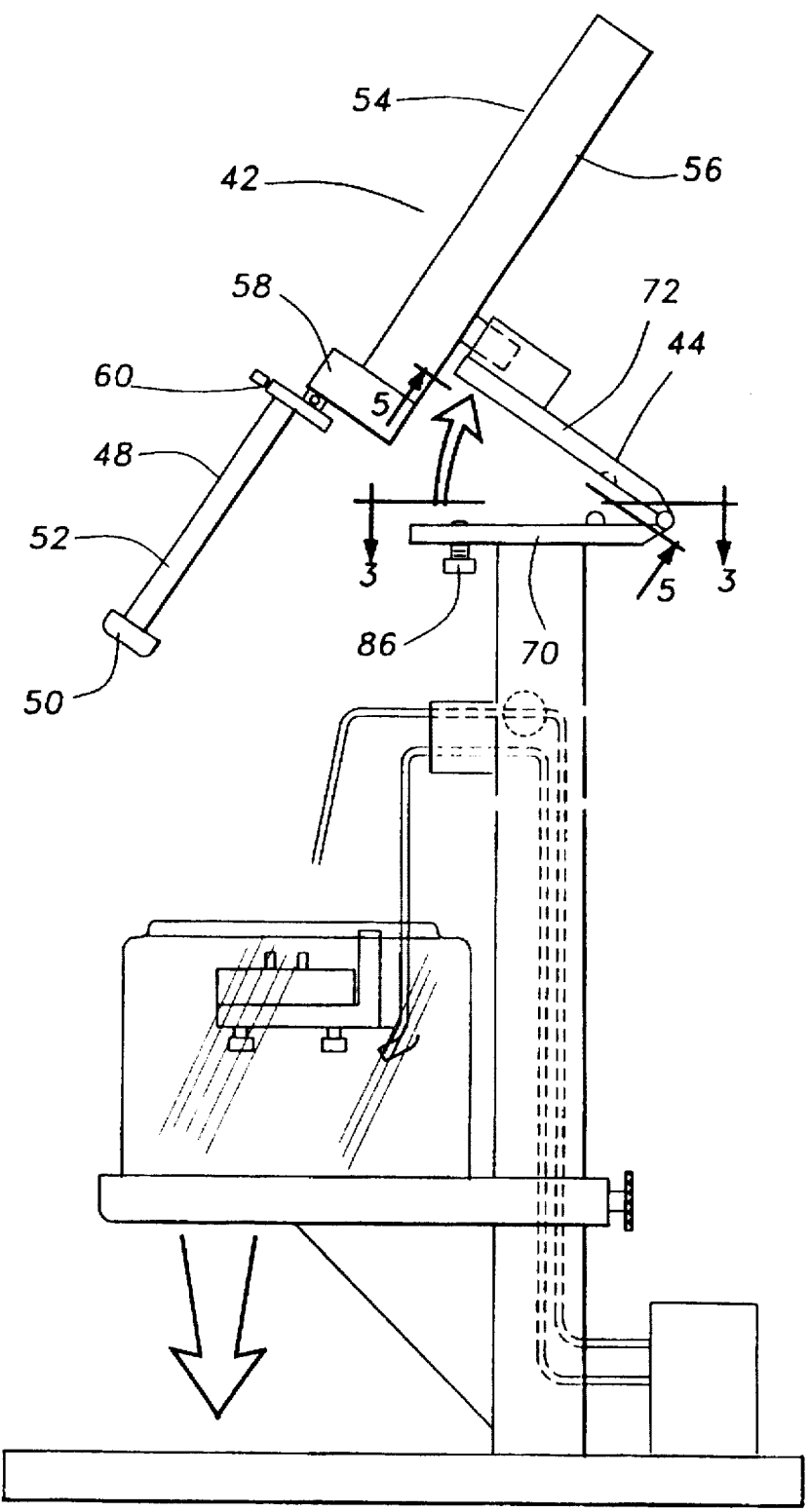
FIG. 2 is a view similar to FIG. 1 but illustrating the device in an inspection position.
Figure 3:
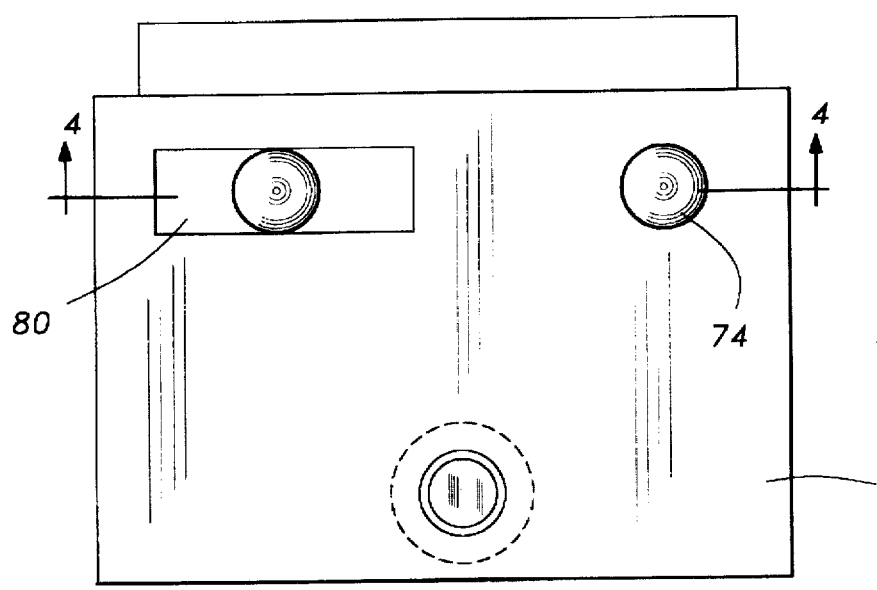
FIG. 3 is a view taken substantially along line 3—3 in FIG. 2.
Figure 4:
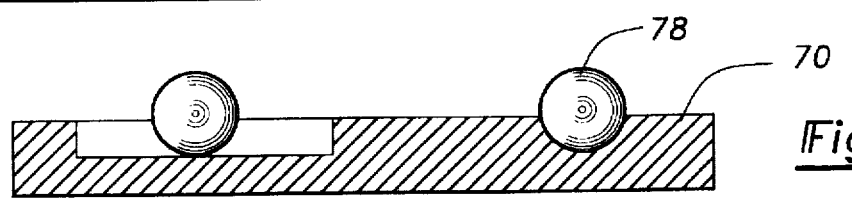
FIG. 4 is a view taken substantially along line 4—4 in FIG. 3.
Figure 5:
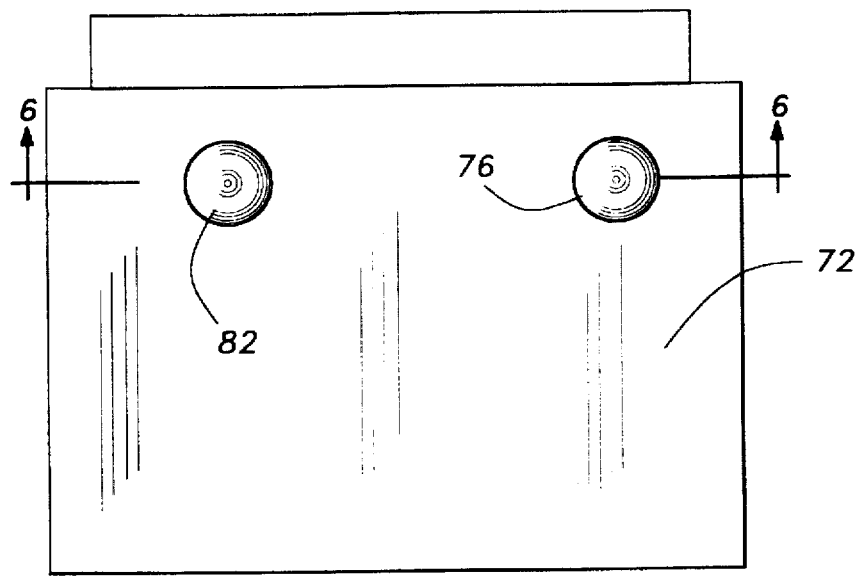
FIG. 5 is a sectional view taken substantially along line 5—5 in FIG. 2.
Figure 6:
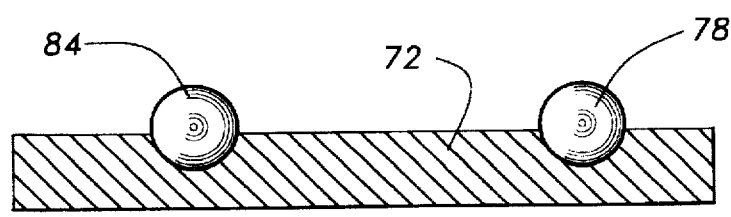
FIG. 6 is a view taken substantially along line 6—6 in FIG. 5.

With reference now to FIGS. 1 and 2, a work holder assembly 42 is pivotally mounted to the top of the vertical support 16 by a hinge assembly 44 which will be subsequently described in greater detail. However, as shown in FIGS. 1 and 2, the hinge assembly 44 enables the work holder assembly 42 to be pivoted between an operable position, illustrated in FIG. 1, and an inspection position, illustrated in FIG. 2.

The work holder assembly 42 includes an elongated work holder 48 which may be of any rigid construction, such as a metallic pipe. A work piece 50, such as dental bridgework, is removably secured to a lower end 52 of the work holder 48.

The work holder assembly 42 further includes a servo motor 54 having a housing 56 which is secured to the hinge 44 and an actuator 58 which is connected via an X-Y positioning stage 60 to the work holder 48.

With the work holder assembly 42 in its operating position illustrated in FIG. 1, activation of the servo motor 54 longitudinally moves the work holder 48 with its attached work piece 50 along a vertical axis 62 in line not only with the tank 24 but also with the EDM electrodes 40.

As best shown in FIG. 1, the X-Y positioning stage 60 is conventional in construction and enables the position of the work holder 48 to be adjusted in two directions which are perpendicular to each other as well as perpendicular to the axis 62.

When the EDM apparatus of the present invention is utilized in dental applications, it is absolutely necessary that the work holder 48 assume the same position each time the hinge 44 is moved to its closed position (FIG. 1). For that reason, the present invention utilizes a kinetic mount as the hinge 44.

With reference now to FIGS. 3–6, the kinetic hinge is there shown in greater detail as comprising a bottom plate 70 and a top plate 72. A semi-spherical recess 74 is provided in the bottom plate 70 which registers with a like shaped semi-spherical recess 76 in the top plate 72. A ball 78 is disposed between the recesses 74 and 76 and is dimensioned so that the plates 70 and 72 are spaced apart from each other.

Similarly, a channel 80 is provided in the bottom plate 70 which registers with a spherical recess 82 in the top plate 72. A ball 84 is positioned between the channel 80 and recess 82.

Lastly, a threaded fastener 86 (FIG. 2) is threadably secured to the bottom plate 70 and abuts against the top plate 72. This threaded fastener 86 thus controls the pivotal position of the plates 70 and 72 relative to each other.

In operation, the ball 78 absolutely fixes one point between the two plates 70 and 72. The other ball 84 locks the rotational position of the plates 70 and 72 relative to each other while the threaded fastener locks the pivotal position of the plates 70 and 72 relative to each other. The kinetic mount thus ensures that, with the hinge assembly 44 in its closed position, the position of the work holder 48 is precise and repeatable.

The electrical discharge apparatus of the present invention is utilized primarily for dental applications in which the bridgework is mounted as the work piece 50 to the work holder 48. The positioning of the bridgework 50 can be precisely positioned through the X-Y positioning stage 60 as well as the adjustment screws 38.

Since the work piece or bridgework 50 is mounted to the work holder 48, the work piece 50 can be easily and rapidly inspected by the dentist or dental technician in the conventional fashion. Appropriate adjustments via the X-Y positioning stage 60 can be made as required to properly position the bridgework 50 relative to the EDM electrodes 40. When the work holder assembly 42 is returned to its operable position (FIG. 1), the kinetic mount or hinge 44 ensures that the position of the work piece 48 will be precisely returned to its prior position.

Figure 7:
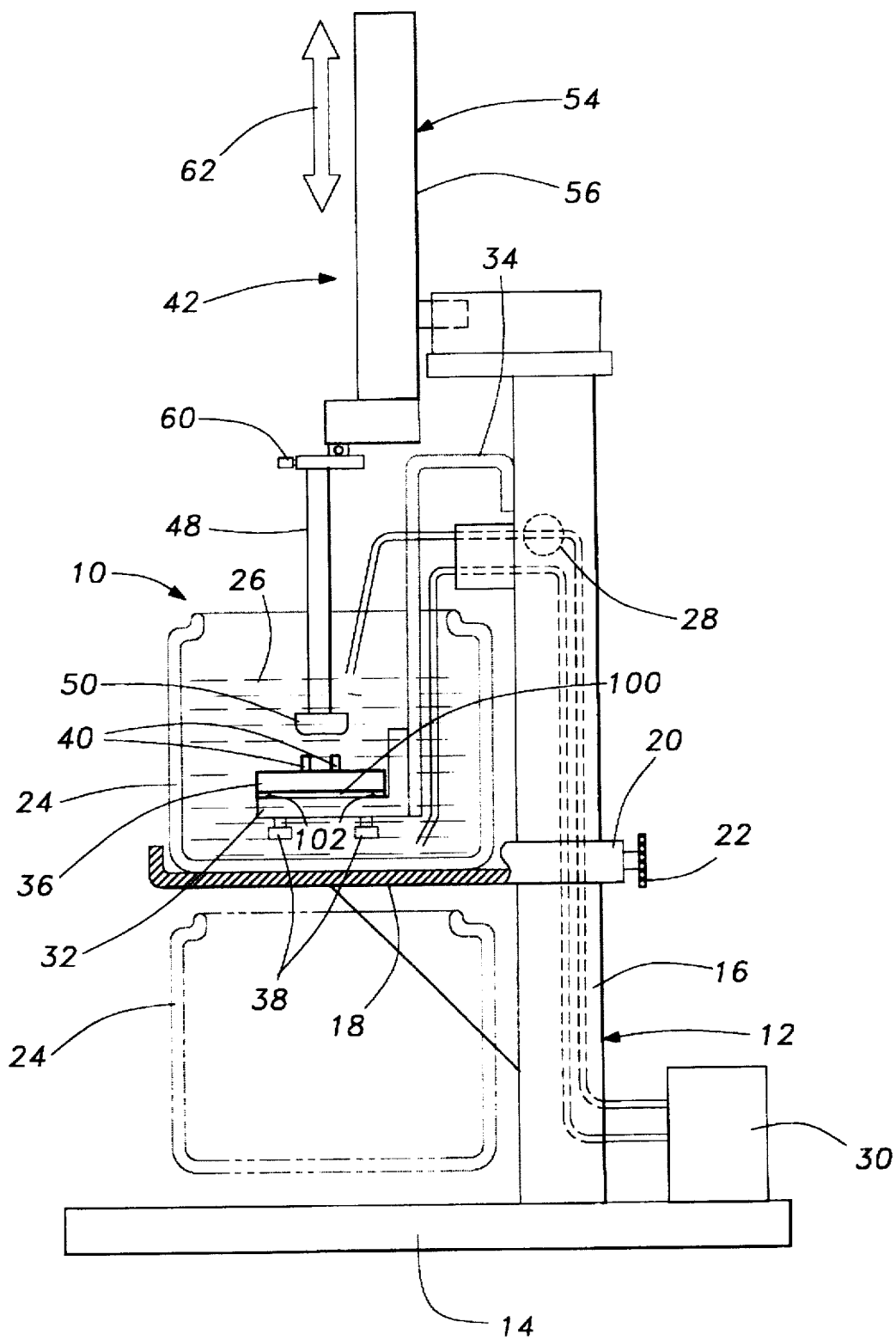
FIG. 7 is a view similar to FIG. 1 but showing a further preferred embodiment of the invention.

With reference now to FIG. 7, a second preferred embodiment of the invention is there shown in which the hinge 44 (FIG. 1) is removed and, instead, the servo motor 54 is secured directly to the frame 12. Activation of the servo motor 54 will, of course, vertically displace the work holder 48 in the desired fashion.

Still referring to FIG. 7, although the X-Y positioning stage 60 (FIG. 1) may be positioned between the servo motor 54 and the work holder 48, optionally or alternatively an X-Y positioning stage 100, including a tilt adjustment mechanism 102, may be positioned between the table 36 and the support 32.

Figure 8:
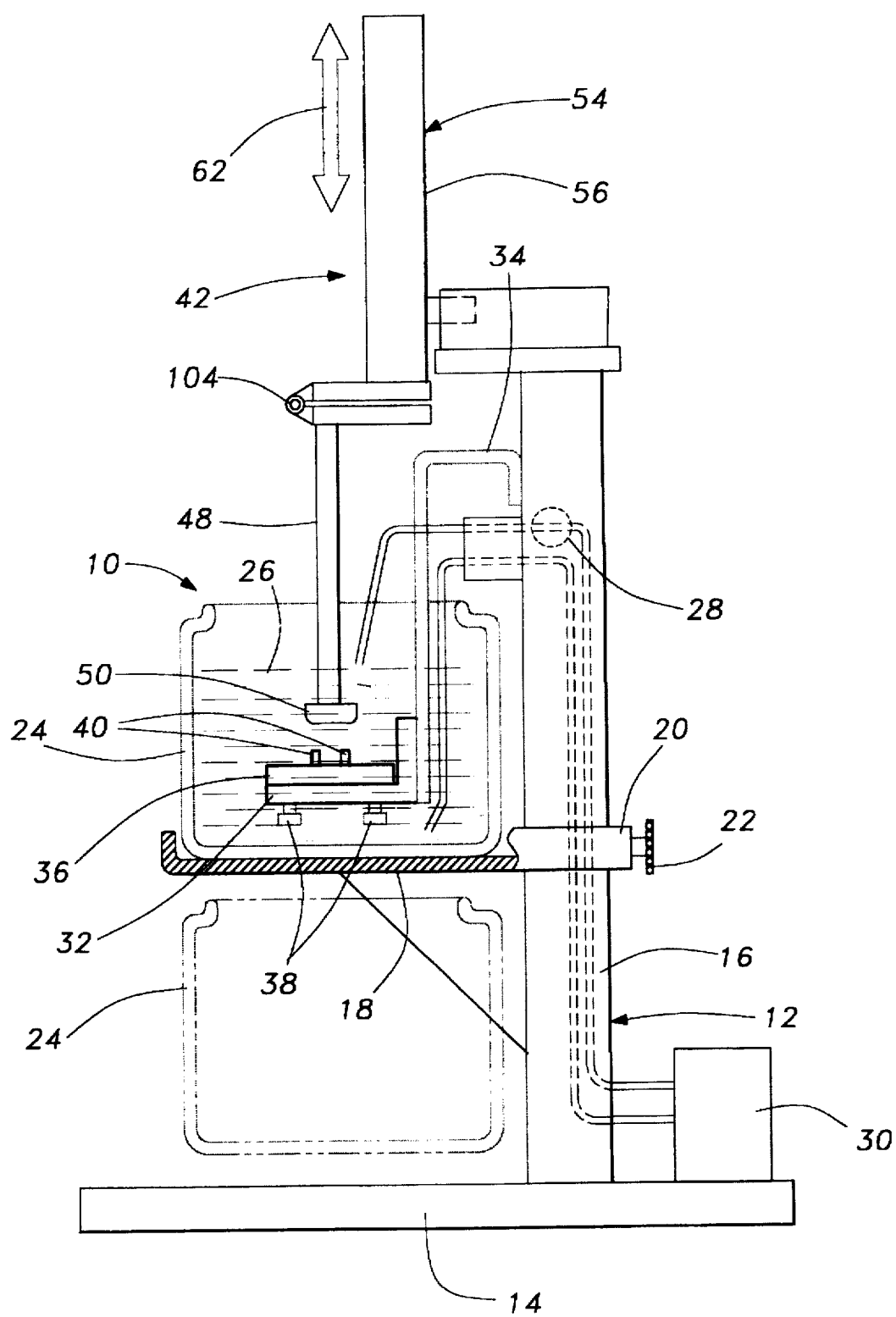
FIG. 8 is a fragmentary view illustrating still a further modification of the invention.

As best shown in FIG. 8, a kinetic hinge assembly 104, similar to the hinge assembly 44, can optionally be positioned between the servo motor 54 and the work holder 48. Such a hinge assembly 104 would allow the technician to remove the work holder 48 with the attached work piece 50 for adjustments away from the EDM apparatus 10 and to subsequently reattach the work holder 48 to the apparatus 10 and accurately reproduce its prior position.

Having described my invention, however, many modifications thereto will become apparent to those skilled in the art to which it pertains without deviation from the spirit of the invention as defined by the scope of the appended claims.

We claim:

1. An electrical discharge machining apparatus comprising:
   a frame having a base and a vertical support secured to and extending upwardly from said base,
   a tank adapted to contain an electrolytic liquid,
   a work holder for holding a part to be machined between a raised position in which a portion of said work holder is positioned in said tank and a lower position in which said work holder is positioned above said tank,
   means for adjustably securing said tank to said vertical support,
   means for adjustably moving said work holder relative to said vertical support along an axis aligned with said tank, and
   electrical discharge machining means secured to said vertical support.

2. The invention as defined in claim 1 and comprising means for cleaning the electrolytic liquid in said tank.

3. The invention as defined in claim 2 wherein said cleaning means comprises a pump and a filter, said pump having an outlet open to said tank and said filter fluidly connected in series between said tank and an inlet to said pump.

4. The invention as defined in claim 1 and comprising means for pivotally securing said work holder to a top of said vertical support so that said work is pivotal between a first position in which the part is aligned with said tank and a second position in which the part is spaced laterally from said tank.

5. The invention as defined in claim 4 wherein said tank securing means comprises means for locking said tank securing means to said vertical support at an adjusted position.

6. The invention as defined in claim 4 wherein said pivotal securing means comprises a kinetic mount.

7. The invention as defined in claim 1 wherein said means for adjustably moving said work holder comprises a servo motor.

8. The invention as defined in claim 1 and comprising means for adjustably securing said electrical discharge machining means within said tank.

9. The invention as defined in claim 1 and comprising means for adjustably moving said work holder in a first direction transverse to said axis aligned with said tank.

10. The invention as defined in claim 9 and comprising means for adjustably moving said work holder in a second direction, said second direction being transverse to both said axis aligned with said tank and said first direction.

11. An electrical discharge machining apparatus comprising:

a frame having a base and a vertical support secured to and extending upwardly from said base, a tank adapted to contain an electrolytic liquid, means for securing said tank to said vertical support, a work holder for holding a part to be machined, means for adjustably moving said work holder relative to said vertical support along an axis aligned with said tank, electrical discharge machining means secured to said vertical support, and means for adjustably moving said electrical discharge machining means in a direction transverse to said axis aligned with said tank.

12. The invention as defined in claim 11 and comprising means for adjustably moving said electrical discharge machining means in a second direction, said second direction being transverse to both said axis aligned with said tank and said first direction.

13. The invention as defined in claim 11 and comprising means for cleaning the electrolytic liquid in said tank.

14. The invention as defined in claim 13 wherein said cleaning means comprises a pump and a filter, said pump having an outlet open to said tank and said filter fluidly connected in series between said tank and an inlet to said pump.

15. The invention as defined in claim 11 and comprising means for pivotally securing said work holder to a top of said vertical support so that said work is pivotal between a first position in which the part is aligned with said tank and a second position in which the part is spaced laterally from said tank.

16. The invention as defined in claim 15 wherein said tank securing means comprises means for locking said tank securing means to said vertical support at an adjusted position.

17. The invention as defined in claim 11 wherein said means for adjustably moving said work holder comprises a servo motor.

18. The invention as defined in claim 11 and comprising a kinetic hinge assembly operatively connected between said moving means and said work holder.

* * * * *